United States Patent [19]

Suss et al.

[11] Patent Number: 4,857,307

[45] Date of Patent: Aug. 15, 1989

[54] ALCOHOL FREE-LIQUID MAKEUP COMPOSITION

[75] Inventors: Harold Suss, Germantown; Virginia F. Ner, Memphis, both of Tenn.

[73] Assignee: Plough, Inc., Memphis, Tenn.

[21] Appl. No.: 121,550

[22] Filed: Nov. 17, 1987

[51] Int. Cl.[4] ...................... A61K 7/021; A61K 7/035
[52] U.S. Cl. ........................................ 424/63; 424/69; 424/401; 514/778
[58] Field of Search .................... 424/63, 69, 128, 401

[56] References Cited

U.S. PATENT DOCUMENTS

| | | |
|---|---|---|
| 3,920,883 | 11/1975 | Yamada et al. ...................... 424/78 |
| 4,115,307 | 9/1978 | McGilvery .......................... 424/128 |
| 4,183,959 | 1/1980 | Wood et al. ........................ 424/69 |
| 4,462,981 | 7/1984 | Smith ................................. 424/401 |
| 4,690,821 | 9/1987 | Smith et al. ....................... 424/401 |
| 4,767,741 | 8/1988 | Komor et al. ...................... 424/78 |

Primary Examiner—Ellis P. Robinson
Assistant Examiner—P. J. Ryan
Attorney, Agent, or Firm—Thomas D. Hoffman; Gerald S. Rosen

[57] ABSTRACT

Liquid makeup compositions containing an oil-absorbing effective amount of distarch phosphate in an alcohol-free e.g. ethanol-free-liquid makeup formulation which may be anhydrous, an oil-in-water emulsion or a water-in-oil emulsion.

5 Claims, No Drawings

ALCOHOL FREE-LIQUID MAKEUP COMPOSITION

BACKGROUND OF THE INVENTION

This invention relates to liquid makeup compositions containing an oil-absorbing effective amount of distarch phosphate in an alcohol-free liquid makeup formulation which may be anhydrous or an oil-in-water emulsion or a water-in-oil emulsion.

The concept of fluid foundation makeups, i.e. the incorporation of a face powder into a liquid vehicle, is old. The main functions of foundation makeups are to hide skin flaws, to leave the skin appearing smoother and to give the illusion of a different face shape. Colored foundation makeup i.e. blushes, incorporate colorants to provide a color, a subtle highlight or glow to the face, especially the cheeks. Numerous attempts have been made to develop makeup products that allow face powder or colored powders to be applied to the skin in the form of a smooth layer. For example, there were developed "grease paints", i.e. foundation makeup in the form of non-flowing pastes or creams as well as suspension products such as "calamine lotion", a suspension of insoluble, inert substances in water. The grease paint products were messy and the suspension products which separated rapidly on standing had to be shaken vigorously before use. There have been improvements in liquid makeups. For example "grease paints" have been replaced by liquid makeup products developed by The House of Westmore wherein various pigments and fillers were incorporated into a vehicle that was non-oily, free-flowing and easily spreadable on the skin with drying. Suspension products, such as "60-40-20", an oil control cleanser product have been sold by Vicks Toiletry Products, Div. of Richardson Merrell, Inc. This suspension product contained phosphate starch, specially denatured (SD) ethanol, clay, zinc oxide and titanium oxide suspended in water.

SUMMARY OF THE INVENTION

The present invention provides a liquid makeup composition comprising an oil-absorbing effective amount of distarch phosphate in an alcohol-free liquid makeup formulation.

DETAILED DESCRIPTION OF THE INVENTION

The liquid makeup compositions of the present invention incorporate an oil-absorbing effective amount of distarch phosphate in an alcohol-free makeup formulation. The alcohol-free formulations may be anhydrous, an oil-in-water emulsion or a water-in-oil emulsion or other stable suspensions.

The term "alcohol-free" as used herein in reference to the compositions of the present invention means substantially free of lower alcohols such as ethanol, specially denatured (SD) ethanol or isopropyl alcohol, and the like.

The term "oil-absorbing effective amount" as used herein in reference to the distarch phosphate means an amount of distarch phosphate, i.e. at least about 1 percent by weight, sufficient to absorb all the oil on the skin to which liquid makeup compositions of the present invention are applied. Ranges for distarch phosphate are normally in the range of about 1 to about 10 percent, preferably about 2 to about 6 percent, more preferably about 3 to about 5 percent by weight of liquid makeup composition.

The liquid makeup compositions of the present invention (1) are relatively fast-drying to allow for an even application on the skin; (2) are non-settling; (3) are stable in storage; (4) have the proper pouring consistency; (5) have a good feel without an undesirable oily, sticky, greasy or watery feel; (6) are relatively durable and resistant to flaking and peeling; and (7) can be formulated to contain the proper blend of colors to achieve a wide range of visual effects.

The materials used in the preparation of alcohol-free makeup formulations used in the liquid makeup compositions of the present invention may be classified into three phases: (1) A color mix or powder phase, (2) an aqueous phase; and (3) an oil phase. Each of these phases can be further divided into several different subgroups.

The color-mix or powder phase typically includes pulverulent materials, fillers, metallic stearates, inorganic colorants, organic lakes, and pearlescent materials. Typical pulverulent materials include titanium dioxide and zinc oxide which provide opacity or coverage on the skin. Zinc oxide and titanium dioxide can also function as sunscreens. Typical fillers include talc which provides some opacity and create a matte effect on the skin. Typical inorganic colorants include the ochres, umbers, siennas, black, yellow and red iron oxides, ultramarine blues and violets. Typical organic lakes includes D&C Red Nos. 6, D&C Red No. 7 and D&C Orange No. 5. Such organic lakes, alone or in combination with one or more inorganic colorants may be included in blush mattes and rouges in concentration sufficient to provide the desired brightness or blush effect. The powder phase may also incorporate pearlescent materials which typically may include bismuth oxychloride, titanium coated mica, natural pearl, mica, crystals of quanine as well as titanated mica. Generally, the pearlescent materials are dispersed in an oily vehicle or the finished emulsion.

The aqueous phase may be divided in several different subgroups such as wetting or dispersing agents, alkalies or bases, gums and clays, polyols, film-forming polymers in addition to water which is the main ingredient in many liquid or cream makeup preparations.

Typical suitable wetting or dispersing agents include lecithin and its derivatives, surfactants such as sodium lauryl sulfate, sulfosuccinates, ethoxylated sorbitan esters, sorbitan stearate and lanolin derivatives. Such dispersing agents greatly facilitate the wetting down of the inorganic colorants and/or organic lakes in the aqueous phase as well as the blending of inorganic colorants and/or organic lakes.

Typical suitable alkalies or bases include triethanolamine, potassium and sodium hydroxide. These bases combine with the fatty acids in the oil phase in situ to form soaps which are primary emulsifiers aiding to wet, disperse and suspend the color mix present, especially the inorganic colorants.

Typical suitable gums and clays are those gums and clays which act as co-emulsifiers, thickeners and suspending agents. Among those commonly used are magnesium aluminum silicate sold under the tradename of Veegum, bentonite, Carbopol, sodium carboxymethylcellulose, methylcellulose, hydroxyethylcellulose, gum arabic, karaya, extract of quince seed, as well as gum tragacanth. Such gums and clays function when used either alone or in combination help in suspending the inorganic colorants and/or organic lakes in the final emulsion. Usually a combination of two or more gums provides a system that exhibits greater viscosity control than when used individually. Most of the synthetic gums are available in several viscosity grades to aid in viscosity control.

Typical suitable polyols include propylene glycol, 1,3-butanediol, sorbitol, glycerin, hexylene glycol, ethoxylated glycerin, polyethylene glycol derivatives or some blend of them. These materials improve the spreadability of the make-up, help control the rate of drying, and add smoothness and creaminess to the finished product. They also aid in stability to freeze-thaw cycles.

Typical suitable film forming polymers include polyvinylpyrrolidone (PVP), polyvinylacetate (PVA), PVP/PVA, cellulose acetate, cellulose acetate butyrate, methyl polyacrylate, methyl polymethacrylate and starch derivatives.

The oil phase includes those materials, both liquid and solid, which facilitate emulsification, spreadability, dispersion of the inorganic colorants and/or organic lake and viscosity control. These materials include fatty acids, waxes, liquid hydrocarbons, oils, fatty acid esters, emulsifying and thickening agents, lanolin and its derivatives, sunscreens as well as antioxidants, preservatives and perfume as well as the distarch phosphate.

Typical suitable fatty acids include stearic acid, oleic acid and undecylenic acid. Waxes commonly used are carnauba, ozokerite, candelilla, microcrystalline wax, lanolin waxes, beeswax and paraffin wax. Liquid hydrocarbons may constitute a major portion of the oil phase and include different mineral oil viscosities, perhydrosqualene and petrolatum of different melting points. Also often used to achieve different spreadability and skin texture effects are oils such as vegetable oils such as sesame, peach kernel, cottonseed, apricot kernel, peanut, corn or avocado. Such oils spread easily, are relatively non-greasy and do not dry out. These oils seem to disappear readily into the skin. Other oils include castor oil, olive oil, acetylated fatty acid monoglycerides and cholesterol as well as silicon oils such as dimethicone, dimethylpolysiloxane and cyclomethicone. Typical suitable fatty acid esters include isopropyl-myristate, -palmitate, -linoleate, -lanolate; butyl oleate; propylene glycol monooleate; propylene glycol monolaurate; butyl stearate; cetyl lactate; myristyl lactate; diethyl sebacate, and myristyl myristate may also be used to replace part of the mineral oil.

Typical suitable emulsifying and thickening agents in the oil phase include cetyl and stearyl alcohols, spermaceti, cetylpalmitic-amide, ethoxylated cetyl-stearyl alcohols, propylene glycol and glyceryl esters, sorbitan and ethoxylated sorbitan esters and their derivatives, diethylene glycol derivatives and many other chemical entities. These materials improve application properties.

Lanolin and its derivatives also play an important role in the oil phase. Effectively used materials such as lanolin, lanolin absorption bases, ethoxylated lanolin, lanolin alcohols, acetylated lanolin, liquid cholesterol derivatives, hydrocarbon lanolin fractions, liquid lanolin and esterified lanolin fractions aid greatly in spreadability, pigment dispersion, deflocculation and emulsification. They promote product adhesion to the skin.

Antioxidants such as propyl gallate, BHA, BHT, tocopherols and others may be incorporated in makeup compositions containing vegetable oils to counteract rancidity on aging.

Preservatives may be included in makeup compositions, especially those containing water.

Typical suitable preservatives include the lower alkyl esters of para-hydroxybenzoates (paraben) especially, methyl paraben, ethyl paraben, n-propyl paraben, isopropyl paraben, n-butyl paraben, isobutyl paraben and mixtures thereof, imidazolidinyl urea, or diazolidinyl urea.

Typical suitable sunscreens include titanium dioxide, certain esters of salicylic acid, e.g. homomenthyl salicylate, alkyl esters of paramethoxycinnamate, e.g. octyl methoxycinnamate and certain benzophenone derivatives, e.g. benzophenone-3 and substitutee para-aminobenzoates e.g. octyl dimethyl PABA.

The liquid makeup compositions of the present invention are alcohol-free and may be either substantially anhydrous or oil-in-water emulsions or water-in-oil emulsions.

By the term "substantially anhydrous" is meant less than about 1 percent by weight water in the total makeup composition. The substantially anhydrous liquid makeup compositions, of course, do not contain a water phase but usually contain a high proportion of low viscosity oils, and waxes. Many of these preparations have incorporated lanolin derivatives and dispersing agents to wet and deflocculate the inorganic colorants and organic lakes which are present at relatively high levels.

A typical anhydrous liquid makeup composition contains about 30-45% by weight of solids (the color mix or powder phase) and about 55-65% by weight of an oil phase. All the ingredients are typically mixed together by use of any of the mixing methods well known to those in the cosmetic arts such as roller mills, colloid mills, homogenizers and the like. Titanium dioxide, red, yellow and black iron oxides and ultramarine blues when used, are micropulverized and then mixed with the other ingredients.

The water-in-oil and oil-in-water emulsion makeup compositions are prepared in a colloid mill. Typically the water phase and color mix phase, which may include the polyols, are mixed until a homogeneous dispersion is formed. The oil phase, including the oil absorbing amount of distarch phosphate, is heated to melt the waxes, when used, and then mixed together until uniform. The oil phase is added to the dispersion of the aqueous or water and color mix phases and mixing is continued until a uniform emulsion is formed. The emulsion is typically cooled and other ingredients such as perfume are added.

The following examples illustrate the invention. Definition and suppliers of the ingredients used may be found in the CTFA Cosmetic Ingredients Dictionary, published in 1982 by the Cosmetic, Toiletry, and Fragrance Association, Inc., 1110 Vermont Avenue, N.W., Washington, D.C. 20005, U.S.A.

| Ingredients | Wgt. % |
| --- | --- |
| Part A | |
| Water | 54.06 |
| Magnesium aluminum silicate | 0.6 |
| Part B | |
| Propylene Glycol | 2.00 |
| sodium carboxymethyl cellulose[1] | 0.10 |
| Part C | |
| Triethanolamine | 1.00 |
| Propylene Glycol | 6.00 |

-continued

| Ingredients | Wgt. % |
| --- | --- |
| Glycerin | 2.50 |
| Part D | |
| Inorganic Colorants | 10.74 |
| Part E | |
| Liqua PAR[2] | 0.60 |
| Part F | |
| Water | 2.00 |
| Part G | |
| Stearic Acid | 2.50 |
| Propylene Glycol Stearate SE | 1.50 |
| Cetyl lactate | 0.40 |
| Lanolin acid | 0.80 |
| Simethicone PL | 0.10 |
| Isopropyl Myristate | 2.00 |
| Homomenthyl Salicylate | 6.00 |
| Distarch Phosphate | 5.00 |
| Part H | |
| Water | 1.50 |
| Imidazolidinyl urea | 0.50 |
| Part I | |
| Perfume | 0.10 |

[1]Cellulose Gum may be substituted
[2]Liqua PAR is a mixture of isopropylparaben, isobutylparaben and butylparaben.

Into a stainless steel steam-jacketed kettle equipped with a double-motion mixer, and containing the water of Part A, gradually add thereto magnesium aluminum silicate of Part A (previously passed through a colloid mill) and mix until a uniform dispersion is formed. In a separate container, mix the ingredients of Part B until a uniform dispersion is formed. Add B to A and mix until uniform. Add ingredients of Part C to uniform mixture of A and B and mix until uniform. Add the color mixture of Part D and mix until a uniform dispersion is formed. Add Part E to the so-formed mixture and mix until uniform. Add the water of Part F thereto and bring the temperature of the so-formed water phase to 174°–178° F. (79°–81° C.). Into a separate stainless steel steam-jacketed kettle equipped with suitable agitation and a heating means, add thereto oil phase of Part G and mix while heating to 174°–178° F. (79°–81° C.) until a uniform solution is formed. Then, add thereto, the distarch phosphate of Part G and mix until uniform. Then to the uniform water phase (Parts A–F) gradually add with mixing, the oil phase and distarch phosphate of Part G and mix until uniform. Cool the so-formed uniform dispersion to 131°–140° F. (55°–60° C.). To a separate stainless steel pot, add the ingredients of Part H and mix until uniform. Add Part H to the uniform dispersion of Parts A–G and mix until uniform. Add the perfume of Part I and mix until uniform. Force cool to 86°–95° F. (30°–35° C.) Adjust color, if necessary. Fill at room temperature into appropriate containers.

| Ingredient | Wgt % |
| --- | --- |
| Part A | |
| Water | 36.55 |
| Magnesium Aluminum Silicate | 1.00 |
| Part B | |
| Propylene Glycol | 6.00 |
| ALCOLEC 4135 | 1.00 |
| LIQUA PAR | 0.50 |
| Part C | |
| Propylene Glycol | 2.00 |
| Sodium Carboxymethylcellulose | 0.20 |
| Part D | |
| Triethanolamine | 0.75 |
| Part E | |
| Light ivory color mix | 15.00 |
| Part F | |
| Water | 12.80 |

-continued

| Ingredient | Wgt % |
| --- | --- |
| Part G | |
| Simethicone PL | 0.10 |
| Sodium Cetearyl Sulfate (Lanette Wax E) | 0.50 |
| Part H | |
| Stearic Acid | 1.50 |
| Stearyl Stearoyl Stearate | 2.00 |
| $C_{12-15}$ alcohols octanoate | 6.00 |
| Homomenthyl Salicylate | 6.00 |
| Distarch Phosphate | 3.00 |
| Part I | |
| Cyclomethicone | 3.00 |
| Part J | |
| Water | 1.50 |
| Imidazolidinyl urea | 0.50 |
| Part K | |
| Perfume | 0.10 |

Into a stainless steel steam-jacketed kettle equipped with a double-motion mixer, add the water of Part A and heat it to a temperature of 78°–80° C. Gradually add thereto magnesium aluminum silicate of Part A (previously passed through a colloid mill) and mix until a uniform dispersion is formed and cool to 70°–75° C. Add B to A and mix until uniform. In a separate container, mix the ingredients of Part C until a uniform dispersion is formed. Add the mixture of Part C to uniform mixture of A and B and mix until uniform. Add thereto Part D and mix until a uniform dispersion is formed. Add Part E to the so-formed mixture and mix until a uniform dispersion is formed. Add the water of Part F thereto and bring the temperature of the so-formed mixture to 75°–80° C. Add the ingredients of Part G to the mixture of A–F and mix and maintain a temperature of 75°–80° C. until uniform. Into a separate stainless steel steam-jacketed kettle equipped with suitable agitation and a heating means, add thereto the oil phase of Part H and mix while heating to 75°–80° C. until a uniform solution is formed. Add thereto, the distarch phosphate of Part H and the silicon oil of Part I and mix until uniform. To the uniform water phase (Parts A–F) gradually add with mixing, the oil phase of Part G and the silicon oil of I and mix until uniform. Force cool the so-formed uniform dispersion to 131°–140° F. (55°–60° C.). To a separate stainless steel pot, add the ingredients of Part J and mix until uniform. Add Part J to the uniform dispersion of Parts A–I and mix until uniform. Add the perfume of Part K and mix until uniform. Cool the mixture to 86°–95° F. (30°–35° C.). Adjust color, if necessary. Fill at room temperature into appropriate containers.

We claim:
1. A liquid makeup composition comprising an oil-absorbing effective amount of distarch phosphate in an alcohol-free liquid makeup formulation wherein the effective oil-absorbing amount of distarch phosphate is in the range of from about 1 to about 10 weight percent of said liquid makeup composition.
2. A liquid makeup composition of claim 1 wherein the alcohol-free makeup formulation is an oil-in-water emulsion.
3. A liquid makeup composition of claim 1 wherein the alcohol-free makeup formulation is a water-in-oil emulsion.
4. A liquid makeup composition of claim 1 wherein the alcohol free makeup formulation contains less than about 1 percent by weight water in the total makeup composition.
5. A liquid makeup composition of claim 1 wherein the effective oil-absorbing amount of distarch phosphate is in the range of about 2 to about 6 percent by weight of said liquid makeup composition.

* * * * *